US010945073B2

(12) United States Patent
Pedersen et al.

(10) Patent No.: US 10,945,073 B2
(45) Date of Patent: *Mar. 9, 2021

(54) HEARING PROTECTION SYSTEM WITH OWN VOICE ESTIMATION AND RELATED METHODS

(71) Applicant: GN HEARING A/S, Ballerup (DK)

(72) Inventors: Søren Pedersen, Ballerup (DK); Pete Websdell, Ballerup (DK)

(73) Assignee: GN Hearing A/S, Ballerup (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/505,460

(22) Filed: Jul. 8, 2019

(65) Prior Publication Data

US 2020/0112789 A1 Apr. 9, 2020

Related U.S. Application Data

(63) Continuation of application No. 16/151,346, filed on Oct. 4, 2018, now Pat. No. 10,462,566.

(30) Foreign Application Priority Data

Nov. 14, 2017 (EP) .................................... 17201658

(51) Int. Cl.
*A61F 11/06* (2006.01)
*H04R 3/00* (2006.01)
(Continued)

(52) U.S. Cl.
CPC .......... *H04R 3/007* (2013.01); *G10L 21/0232* (2013.01); *G10L 25/78* (2013.01);
(Continued)

(58) Field of Classification Search
CPC ....................................................... A61F 11/06
See application file for complete search history.

(56) References Cited

U.S. PATENT DOCUMENTS 6,072,884 A * 6/2000 Kates .................. H04R 25/453 381/318
10,142,745 B2 * 11/2018 Petersen .............. H04R 25/552
(Continued)

FOREIGN PATENT DOCUMENTS

EP 2 242 289 A1 10/2010
EP 3 188 507 A1 7/2017

OTHER PUBLICATIONS

EESR dated Apr. 30, 2018 for corresponding EP Application No. 17201658.6.

(Continued)

*Primary Examiner* — Olisa Anwah
(74) *Attorney, Agent, or Firm* — Vista IP Law Group, LLP

(57) ABSTRACT

The present disclosure provides a hearing protection system and a method for estimating a voice signal of a hearing protection system user. The hearing protection system comprises an ear canal microphone for provision of an ear canal input signal; a receiver for provision of an audio output signal; a compensation module for receiving and filtering the ear canal output signal for provision of a compensation signal; and a mixer connected to the ear canal microphone and the compensation module for provision of a voice signal, wherein the compensation module comprises a filter controller, a primary filter and a secondary filter, wherein the primary filter is a static filter, wherein primary filter coefficients of the primary filter are static, and wherein the secondary filter is an adaptive filter, wherein secondary filter coefficients of the secondary filter are controlled by the filter controller based on the voice signal.

34 Claims, 6 Drawing Sheets

(51) Int. Cl.
*H04R 1/10* (2006.01)
*G10L 21/0232* (2013.01)
*G10L 25/78* (2013.01)
*G10L 21/0216* (2013.01)

(52) U.S. Cl.
CPC .. *H04R 1/1016* (2013.01); *G10L 2021/02165* (2013.01); *H04R 1/1083* (2013.01); *H04R 2201/107* (2013.01)

(56) References Cited

U.S. PATENT DOCUMENTS

| | | | | |
|---|---|---|---|---|
| 2009/0034765 | A1 | 2/2009 | Boillot et al. | |
| 2016/0192089 | A1 * | 6/2016 | Merks | H04R 25/505 381/317 |

OTHER PUBLICATIONS

Non-Final Office Action dated Jan. 7, 2019 for related U.S. Appl. No. 16/151,346.

Notice of Allowance and Fee(s) dated Jun. 18, 2019 for related U.S. Appl. No. 16/151,346.

* cited by examiner

HEARING PROTECTION SYSTEM WITH OWN VOICE ESTIMATION AND RELATED METHODS

RELATED APPLICATION DATA

This application is a continuation of U.S. patent application Ser. No. 16/151,346 filed on Oct. 4, 2018, now U.S. Pat. No. 10,462,566, which claims priority to, and the benefit of, European Patent Application No. 17201658.6 filed on Nov. 14, 2017. The entire disclosures of both of the above applications are expressly incorporated by reference herein.

FIELD

The present disclosure relates to a hearing protection system and related methods including a method of estimating a voice signal.

BACKGROUND

In noisy environments, it may be desirable for a user to protect his/her hearing while enabling the user to communicate with others via radio communication. Further, it may be challenging to pick up and separate the user's own voice from the sounds of the environment and/or audio played by a receiver of the hearing protection system.

SUMMARY

Accordingly, there is a need for hearing protection devices and methods with improved estimation and/or detection of a user voice signal of a user of the hearing protection device.

A hearing protection system is disclosed, the hearing protection system comprising an ear canal microphone for provision of an ear canal input signal; a receiver for provision of an audio output signal based on an ear canal output signal; a compensation module for receiving and filtering the ear canal output signal for provision of a compensation signal; and a mixer connected to the ear canal microphone and the compensation module for provision of a voice signal based on the ear canal input signal and the compensation signal. The compensation module comprises a filter controller, a primary filter and a secondary filter. The primary filter may be a static filter, wherein primary filter coefficients of the primary filter are static. The secondary filter may be an adaptive filter, wherein secondary filter coefficients of the secondary filter are controlled by the filter controller, e.g. based on the voice signal.

Further, a method for estimating a voice signal of a hearing protection system user is disclosed, the method comprising providing an audio output signal based on an ear canal output signal; obtaining an ear canal input signal with an ear canal microphone; providing a compensation signal based on the ear canal output signal; and providing a voice signal based on the ear canal input signal and the compensation signal. Providing a compensation signal optionally comprises filtering the ear canal output signal with a primary filter and a secondary filter. The primary filter may be a static filter and the secondary filter may be an adaptive filter.

It is an advantage of the present disclosure that power-efficient own voice estimation is provided while maintaining an accurate own voice estimation.

Further, the present disclosure presents methods, systems and devices that more accurately estimate a user's own voice while retaining a shorter filter length.

It is an advantage of the present disclosure that the response of the playback path including receiver, ear canal microphone and acoustic ear response is precisely modelled. Further, it is an important advantage that the own voice estimation can handle varying or different operating conditions that change over time, even for the same user.

Further, a combination of a static primary filter and an adaptive secondary filter, reduces or eliminates the risk of numerical saturation in the adaptive filter, in turn meaning less computation and a simpler adaptive filter.

It is an advantage of the present disclosure that the adaptive filter converges faster due to the reduced number of taps. Thus, a faster own voice estimation is provided.

A hearing protection system includes: an ear canal microphone configured to provide an ear canal input signal; a receiver configured to provide an audio output signal based on an ear canal output signal; a compensation module configured to receive and to filter the ear canal output signal for obtaining a compensation signal; and a mixer connected to the ear canal microphone and the compensation module, the mixer configured to provide a voice signal based on the ear canal input signal and the compensation signal; wherein the compensation module comprises a filter controller, a primary filter and a secondary filter, wherein the primary filter is a static filter, wherein primary filter coefficients of the primary filter are static, wherein the secondary filter is an adaptive filter, and wherein the filter controller is configured to control secondary filter coefficients of the secondary filter based on the voice signal.

Optionally, the primary filter is an Infinite Impulse Response (IIR) filter.

Optionally, the secondary filter is a Finite Impulse Response (FIR) filter.

Optionally, the hearing protection system further includes a hearing protection processing module and an external microphone, the hearing protection processing module connected to the external microphone for receiving an external input signal from the external microphone, wherein the hearing protection processing module is configured to provide an external output signal based on the external input signal, and wherein the ear canal output signal is based on the external output signal.

Optionally, the primary filter coefficients are for modeling electroacoustic properties of the receiver and the ear canal microphone.

Optionally, the primary filter coefficients are for modeling acoustic properties of a sealed ear canal.

Optionally, the primary filter has a constant first gain in a first frequency range from 100 Hz to 500 Hz.

Optionally, the primary filter has a maximum gain in a second frequency range from 4 kHz to 8 kHz.

Optionally, the primary filter has a local minimum gain in a third frequency range from 1 kHz to 2 kHz.

Optionally, the primary filter has a linearly increasing gain in a fourth frequency range from 30 Hz to 50 Hz.

Optionally, the primary filter has a maximum gain in a frequency range from 4 kHz to 8 kHz.

Optionally, the primary filter has a local minimum gain in a frequency range from 1 kHz to 2 kHz.

Optionally, the primary filter has a linearly increasing gain in a frequency range from 30 Hz to 50 Hz.

Optionally, the filter controller comprises a voice detector configured to detect if a user's own voice is present, and wherein the filter controller is configured to deactivate adaptation of the secondary filter coefficients if the voice detector detects a presence of the user's own voice.

Optionally, the filter controller is configured to activate adaptation of the secondary filter coefficients if the voice detector detects the presence of the user's own voice.

A method for providing a voice signal in a hearing protection system, includes: providing an audio output signal based on an ear canal output signal; obtaining an ear canal input signal with an ear canal microphone; providing a compensation signal based on the ear canal output signal; and providing a voice signal based on the ear canal input signal and the compensation signal; wherein the act of providing the compensation signal comprises filtering the ear canal output signal with a primary filter and a secondary filter, wherein the primary filter is a static filter and the secondary filter is an adaptive filter.

Optionally, the act of providing the compensation signal comprises adapting secondary filter coefficients of the secondary filter based on the voice signal.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
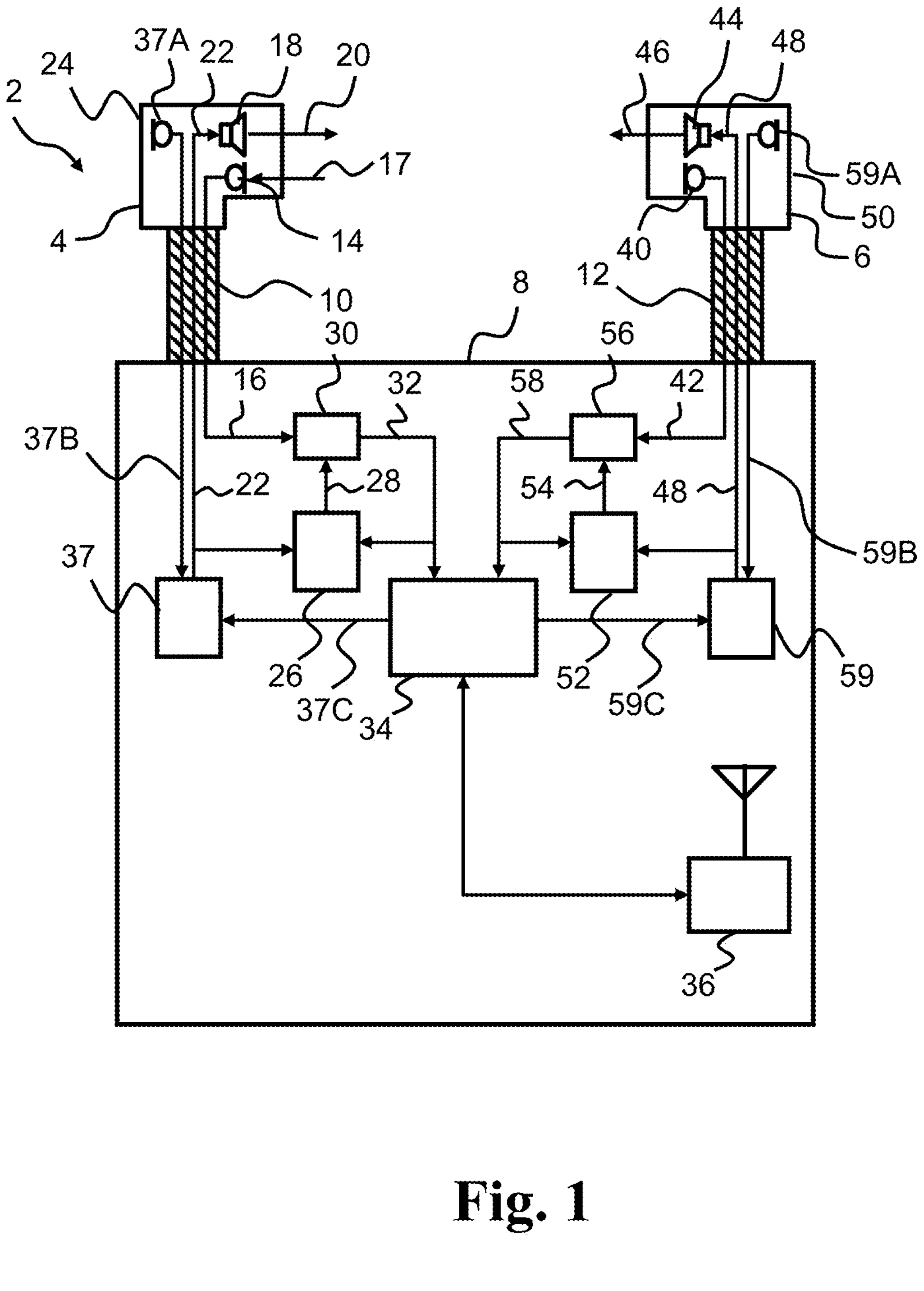
FIG. 1 schematically illustrates an exemplary hearing protection device according to the disclosure, FIG. 2 schematically illustrates an exemplary compensation module, FIG. 3 schematically illustrates an exemplary compensation module.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing protection system is disclosed. The hearing protection system comprises a processing device and one or more earpieces including a first earpiece and/or a second earpiece. The processing device is optionally wired to a first earpiece and a second earpiece. The processing device may be configured to be worn on the body, e.g. torso, arm or leg, of the user. The processing device may be configured to be attached to or integrated in a helmet.

An earpiece, such as first earpiece and/or second earpiece, comprises an earpiece housing. The earpiece housing may be configured for positioning in the ear of a user, such as in the concha and in the ear canal. The earpiece housing optionally comprises an ear canal portion and an outer ear portion. The ear canal portion extends along an ear canal axis, the ear canal portion having a first end. The first end of the ear canal portion points towards the eardrum of a user when the earpiece is inserted into the ear of a user. An ear canal opening may be arranged at the first end of the ear canal portion. The ear canal opening allows sounds to exit/enter the earpiece housing. A plurality of ear canal openings may be provided in the earpiece housing, e.g. to separate receiver sound and ear canal microphone sound. The ear canal opening(s) of the earpiece may each have a diameter in the range from 0.5 mm to 3 mm. The same or different diameters may be applied for different ear canal openings. The ear canal portion may have a length (measured along the ear canal axis) in the range from 2 mm to 20 mm. In one or more exemplary earpieces, the ear canal portion has a length in the range from 3 mm to 15 mm. Thereby, the ear canal wall of the user can be used for fixating the earpiece in the ear canal and/or the ear canal can be sealed near the tympanic membrane on the inner surface of the ear canal. An earpiece may be a hearing protector. Thus, earpiece, such as first earpiece and/or second earpiece, may comprise a protection element, e.g. for forming a seal between the ear canal wall and the ear canal portion (when inserted in the ear canal of the user). The protection element may be made of or comprise foamed polymer. The protection element may circumvent the ear canal portion. The protection element may have a length (extension along the ear canal axis) of at least 2 mm.

The hearing protection system comprises an ear canal microphone, e.g. first ear canal microphone, for provision of an (first) ear canal input signal. An ear canal microphone is optionally configured to detect ear canal audio or sound via an ear canal opening in the earpiece housing. In one or more exemplary hearing protection systems, the hearing protection system comprises a first ear canal microphone and/or a second ear canal microphone for provision of respective first ear canal input signal and second ear canal input signal. The ear canal microphone may be arranged in an earpiece housing of an earpiece. For example, the first ear canal microphone is arranged in first earpiece housing of the first earpiece and the second ear canal microphone is arranged in second earpiece housing of the second earpiece. The first earpiece may be configured for a left ear of a user and the second earpiece may be configured for a right ear of a user or vice versa.

The hearing protection system comprises a receiver, e.g. first receiver, for provision of an (first) audio output signal based on an (first) ear canal output signal. In one or more exemplary hearing protection systems, the hearing protection system comprises a first receiver and/or a second receiver for provision of respective first audio output signal and second audio output signal based on respective first ear canal output signal and second ear canal output signal. For example, the first receiver is arranged in first earpiece housing of the first earpiece and/or the second ear canal microphone is arranged in second earpiece housing of the second earpiece. A receiver may provide the audio output signal via the ear canal opening in the ear canal portion or via an output port in the ear canal portion.

The hearing protection system comprises a compensation module for receiving and filtering the (first) ear canal output signal for provision of a (first) compensation signal. The compensation module may be arranged in processing device of the hearing protection system. The compensation module may be for receiving and filtering a second ear canal output signal for provision of a second compensation signal.

The hearing protection system comprises a (first) mixer. The (first) mixer is connected to the (first) ear canal microphone and the compensation module for provision of a (first) voice signal based on the (first) ear canal input signal and the (first) compensation signal. The hearing protection system may comprise a second mixer. The second mixer may be connected to the second ear canal microphone and the compensation module for provision of a second voice signal based on the second ear canal input signal and the second compensation signal. The first mixer and/or the second mixer may be arranged in processing device of the hearing protection system. A mixer may be configured to subtract the compensation signal from the ear canal input signal. For example, the first mixer may be configured to subtract the first compensation signal from the first ear canal input signal. The second mixer may be configured to subtract the second compensation signal from the second ear canal input signal.

The hearing protection system may comprise a communication unit and a wireless transceiver unit. The communication unit may be configured for processing and/or transmission of first and/or second voice signals via the wireless transceiver unit. The communication unit may be configured for receiving and/or processing of communication signals via the wireless transceiver unit.

The compensation module may comprise a (first) filter controller, a (first) primary filter and a (first) secondary filter. The (first) primary filter may be a static filter, wherein (first) primary filter coefficients of the (first) primary filter are static. The (first) secondary filter may be an adaptive filter, e.g. wherein (first) secondary filter coefficients of the (first) secondary filter are controlled by the (first) filter controller based on the voice signal and/or a (first) primary filter output signal from the (first) primary filter. The (first) filter controller has an input, wherein the input may be connected to the (first) mixer for receiving the (first) voice signal as an input to the (first) filter controller. The (first) filter controller has an input, wherein the input may be connected to the (first) primary filter for receiving the (first) primary filter output signal as an input to the (first) filter controller.

The (first) filter controller may comprise an own voice detector configured to detect if a user's own voice is present. The (first) filter controller may be configured to forgo, stop or deactivate adaptation of the (first) secondary filter coefficients in accordance with the own voice detector detecting presence of the user's own voice. The (first) filter controller may be configured to start or activate adaptation of the (first) secondary filter coefficients in accordance with the own voice detector detecting absence of the user's own voice. Thereby adaptation on the user's own voice is avoided or at least reduced, further improving the own voice estimation and power efficiency. A further benefit of an improved own voice estimate is that comb filter effects in the voice signal, which may be present when the hear-thru path is active, are reduced.

The (first) filter controller may be configured to determine if a filter adaption criterion is met. The (first) filter controller may be configured to start or activate adaptation of the (first) secondary filter coefficients in accordance with the filter adaption criterion being met. The (first) filter controller may be configured to forgo, stop or deactivate adaptation of the (first) secondary filter coefficients in accordance with the filter adaption criterion not being met. To determine if a filter adaption criterion is met may comprise determining if the first output signal from the communication unit and/or the first ear canal input signal (or first compensation signal) comprises tonal inputs (e.g. if a tonal parameter indicative of tonal content is larger than a tonal threshold) and wherein the filter adaption criterion is not met if the first output signal from the communication unit and/or the first ear canal input signal (or first compensation signal) comprises tonal inputs.

The compensation module may comprise a second filter controller, a second primary filter and a second secondary filter. The second primary filter may be a static filter, wherein second first primary filter coefficients of the second primary filter are static. The second secondary filter may be an adaptive filter, e.g. wherein second secondary filter coefficients of the second secondary filter are controlled by the second filter controller based on the voice signal and/or a second primary filter output signal from the second primary filter. The second filter controller has an input, wherein the input may be connected to the second mixer for receiving the second voice signal as an input to the second filter controller. The second filter controller has an input, wherein the input may be connected to the second primary filter for receiving the second primary filter output signal as an input to the second filter controller.

The second filter controller may comprise an own voice detector configured to detect if a user's own voice is present. The second filter controller may be configured to forgo, stop or deactivate adaptation of the second secondary filter coefficients in accordance with the own voice detector detecting presence of the user's own voice. The second filter controller may be configured to start or activate adaptation of the second secondary filter coefficients in accordance with the own voice detector detecting absence of the user's own voice.

The second filter controller may be configured to determine if a filter adaption criterion is met. The second filter controller may be configured to start or activate adaptation of the second secondary filter coefficients in accordance with the filter adaption criterion being met. The second filter controller may be configured to forgo, stop or deactivate adaptation of the second secondary filter coefficients in accordance with the filter adaption criterion not being met. To determine if a filter adaption criterion is met may comprise determining if the second output signal from the communication unit and/or the second ear canal input signal (or second compensation signal) comprises tonal inputs (e.g. if a tonal parameter indicative of tonal content is larger than a tonal threshold) and wherein the filter adaption criterion is not met if the second output signal from the communication unit and/or the second ear canal input signal (or second compensation signal) comprises tonal inputs.

A combination of a static filter and an adaptive filter in the compensation module provides an increased accuracy of the playback model, and thus an improved and/or faster own voice estimate, while using less coefficients in the first filter and/or in the adaptive secondary filter, in turn improving (reducing) power consumption.

Further, the present disclosure allows for a reduced gain in the adaptive secondary filter, as it is only required to model the difference between primary filter and playback transfer function, thus simplifying the real-time operation of the adaptive secondary filter.

Further, the combination of a static filter and an adaptive filter in the compensation module provides the ability to detect reduced low frequency gain in the adaptive secondary filter, which may lead to improved detection of a poor earpiece seal.

A primary filter, such as first primary filter and/or second primary filter, may be an Infinite Impulse Response (IIR) filter. A primary filter may be of N'th order, e.g. where N is an integer in the range from 3 to 15, such as in the range from 4 to 10, for example 6 or 8. An IIR implementation of the primary filter(s) is advantageous in that IIR filters are able to represent common features of the playback path (receiver, ear canal microphone, and/or acoustic properties of ear canal) using much fewer coefficients/lower order.

The (first) primary filter coefficients may model electroacoustic properties of the (first) receiver and/or the (first) ear canal microphone. The second primary filter coefficients may model electroacoustic properties of the second receiver and/or the second ear canal microphone.

The (first) primary filter coefficients may model acoustic properties of an ear canal, such as a sealed ear canal. The second primary filter coefficients may model acoustic properties of an ear canal, such as a sealed ear canal.

A primary filter, such as the first primary filter and/or the second primary filter may have a constant first gain or substantially constant first gain (±0.5 dB) in a first frequency range. The first frequency range may be from 100 Hz to 500 Hz.

A primary filter, such as the first primary filter and/or the second primary filter may have a maximum gain in a second frequency range. The second frequency range may be separate from the first frequency range. The second frequency range may be from 4 kHz to 8 kHz.

A primary filter, such as the first primary filter and/or the second primary filter may have a local minimum gain in a third frequency range. The third frequency range may be separate from the first frequency range. The third frequency range may be separate from the second frequency range. The third frequency range may be from 1 kHz to 2 kHz.

A primary filter, such as the first primary filter and/or the second primary filter may have a linearly increasing gain in a fourth frequency range in the range from 30 hz to 50 Hz.

The secondary filter, such as first secondary filter and/or second secondary filter, may be a Finite Impulse Response (FIR) filter. The number of secondary taps/secondary coefficients, e.g. of the first secondary filter and/or the second secondary filter, may be less than 40, such as in the range from 20 to 38.

The hearing protection system may comprise a hearing protection processing module and (first) external microphone. The hearing protection processing module may be connected to the (first) external microphone for receiving (first) external input signal from the (first) external microphone and configured to provide (first) output signal based on the (first) external input signal. The (first) ear canal output signal may be based on the (first) external output signal. The hearing protection processing module may be arranged in the processing device of the hearing protection system. The first external microphone may be arranged in first earpiece housing of the first earpiece. An external microphone is arranged in earpiece housing of an earpiece and configured to pick up external or ambient sounds.

The hearing protection system may comprise a second external microphone. The hearing protection processing module may be connected to the second external microphone for receiving second external input signal from the second external microphone and configured to provide second external output signal based on the second external input signal. The second ear canal output signal may be based on the second external output signal. The second external microphone may be arranged in second earpiece housing of the second earpiece.

Also disclosed is a method for estimating a voice signal of a hearing protection system user. The method comprises providing an audio output signal based on an ear canal output signal, e.g. with a receiver of an earpiece inserted in the ear canal of a user. The earpiece may seal, shield or close the ear canal. In other words, the earpiece may attenuate external sound at least 10 dB. The method comprises obtaining an ear canal input signal with an ear canal microphone, e.g. of the earpiece inserted in the ear canal of the user. The method comprises providing a compensation signal based on the ear canal output signal, e.g. with a compensation module as described herein. The method comprises providing a voice signal based on the ear canal input signal and the compensation signal. Providing a compensation signal comprises filtering the ear canal output signal with a primary filter, e.g. as disclosed herein, and a secondary filter, e.g. as disclosed herein, wherein the first filter is optionally a static filter and/or the second filter is optionally an adaptive filter. Providing a compensation signal may comprise adapting secondary filter coefficients of the secondary filter based on the voice signal. Providing a compensation signal may comprise detecting presence of an own voice of the user and optionally forgo, stop or de-activate adapting secondary filter coefficients of the secondary filter if an own voice of the user is detected. In one or more exemplary methods, presence of an own voice of the user is detected based on the voice signal, e.g. if a voice signal parameter is larger than a first threshold. Providing a compensation signal may comprise determining if an adaptation criterion is fulfilled, e.g. based on the voice signal, and optionally adapting secondary filter coefficients of the secondary filter based on the voice signal if the adaptation criterion is fulfilled. The adaptation criterion may be fulfilled if no own voice of the user is detected, e.g. with an own voice detector.

Providing a compensation signal comprises filtering the ear canal output signal with a primary filter and secondary filter to obtain a secondary filter output signal also denoted compensation signal. Providing a compensation signal may comprise adapting secondary filter coefficients of the secondary filter based on the secondary filter output signal/compensation voice signal.

The method or at least parts thereof may be performed by a hearing protection system as disclosed herein.

FIG. 1 schematically shows an exemplary hearing protection system 2 comprising a first earpiece 4, a second earpiece 6 and a processing device 8. The first earpiece 4 is connected to the processing device with first cable 10 and the second earpiece 6 is connected to the processing device 8 with second cable 12.

The hearing protection system 2 comprises an ear canal microphone (first ear canal microphone 14) for provision of an ear canal input signal (first ear canal input signal 16) based on first ear canal audio 17 detected by the first ear canal microphone 14. The hearing protection system 2 comprises a receiver (first receiver 18) for provision of an audio output signal (first audio output signal 20) based on an ear canal output signal (first ear canal output signal 22). The first ear canal microphone 14 and the first receiver 18 are arranged in first earpiece housing 24 of the first earpiece 4.

The hearing protection system 2 comprises a compensation module (first compensation module 26) for receiving and filtering the ear canal output signal (first ear canal output signal 22) for provision of a compensation signal (first compensation signal 28).

The hearing protection system 2 comprises a mixer (first mixer 30) connected to the ear canal microphone (first ear canal microphone 14) and the compensation module (first compensation module 26) for provision of a voice signal (first voice signal 32) based on the ear canal input signal (first ear canal input signal 16) and the compensation signal (first compensation signal 28). The voice signal (first voice signal 32) is fed to communication unit 34 for further processing and/or transmission via wireless transceiver unit 36 configured to receive and/or transmit wireless signals.

The hearing protection system 2 comprises a first hearing protection processing module 37 and first external microphone 37A. The first hearing protection processing module 37 is arranged in the processing device 8 and first external microphone 37A is arranged in the first earpiece housing 24. The first hearing protection processing module 37 is connected to the first external microphone 37A for receiving first external input signal 37B from the first external microphone 37A and configured to provide first external output signal based on the first external input signal 37B. The first ear canal output signal 22 may be based on the first external output signal 37B and/or a first output signal 37C from the communication unit 34. The first ear canal output signal 22 may be a sum of the first external output signal 37B and the first output signal 37C from the communication unit 34.

The hearing protection system 2 comprises a second ear canal microphone 40 for provision of a second ear canal input signal 42 based on second ear canal audio 43 detected by the second ear canal microphone 40. The hearing protection system 2 comprises a second receiver 44 for provision of a second audio output signal 46 based on a second ear canal output signal 48. The second ear canal microphone 40 and the second receiver 44 are arranged in second earpiece housing 50 of the second earpiece 6.

The hearing protection system 2 comprises a second compensation module 52 for receiving and filtering the second ear canal output signal 48 for provision of a second compensation signal 54.

The hearing protection system 2 comprises a second mixer 56 connected to the second ear canal microphone 40 and the second compensation module 52 for provision of a second voice signal 58 based on the second ear canal input signal 42 and the second compensation signal 54. The second voice signal 58 is fed to communication unit 34 for further processing and/or transmission via wireless transceiver unit 36 configured to receive and/or transmit wireless signals.

The hearing protection system 2 optionally comprises a second hearing protection processing module 59 and second external microphone 59A. The second hearing protection processing module 59 is arranged in the processing device 8 and second external microphone 59A is arranged in the second earpiece housing 50. The second hearing protection processing module 59 is connected to the second external microphone 59A for receiving second external input signal 59B from the second external microphone 59A and configured to provide second external output signal based on the second external input signal 59B. The second ear canal output signal 48 may be based on the second external output signal 59B and/or a second output signal 59C from the communication unit 34. The second ear canal output signal 48 may be a sum of the second external output signal 59B and the second output signal 59C from the communication unit 34. The first hearing protection processing module 37 and the second hearing protection processing module 59 may be embedded in a single hearing protection processing module or embedded in the communication unit 34

Figure 2:
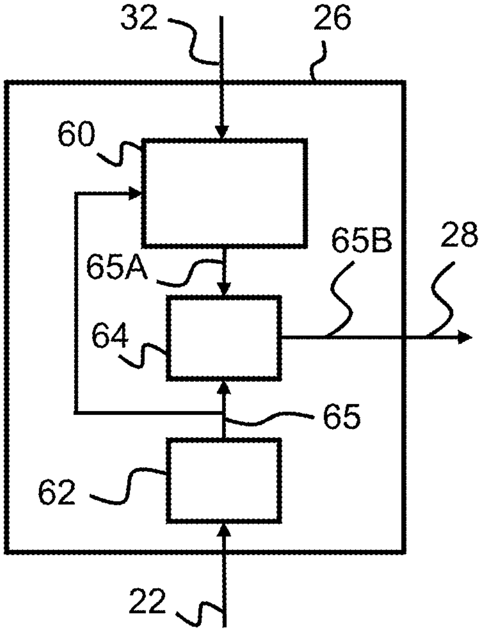

FIG. 2 is a block diagram of an exemplary compensation module e.g. used as first compensation module. The (first) compensation module 26 comprises a first filter controller 60, a first primary filter 62 and a first secondary filter 64. The first filter controller 60 receives the first voice signal 32 and the first compensation signal 28. The first primary filter 62 receives and filters the first ear canal output signal 22 and feeds a primary filter output signal 65 to the first secondary filter 64 and the first filter controller 60. The first secondary filter 64 filters the primary filter output signal 65 according to first control signal 65A from the first filter controller 60 and feeds a secondary filter output signal 65B as output from the first compensation module (first compensation signal 28). The first control signal 65A sets or controls primary filter coefficients of the first secondary filter 64. The first primary filter 62 is a static Infinite Impulse Response (IIR) filter, wherein primary filter coefficients of the first primary filter 62 are static. The first secondary filter 64 is an adaptive Finite Impulse Response (FIR) filter. The combination of an IIR filter and a FIR filter provides a power-efficient and improved modelling of the ear canal response. Secondary filter coefficients of the first secondary filter 64 are controlled by the first filter controller 60 based on the first voice signal 32 and the primary filter output signal 65 from the first primary filter 62.

Figure 3:
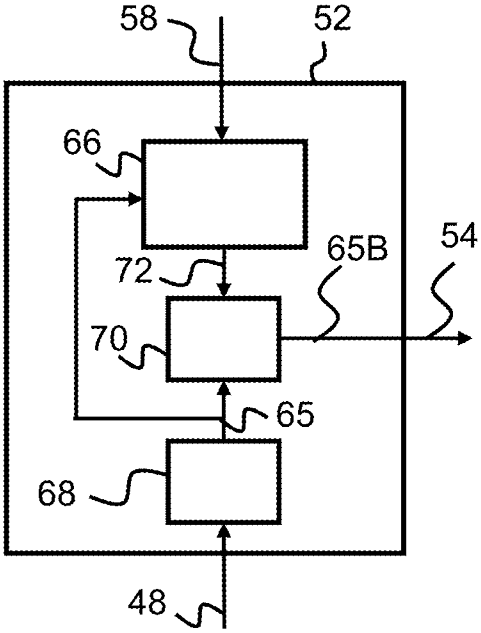

FIG. 3 is a block diagram of an exemplary compensation module e.g. used as second compensation module. The second compensation module 52 comprises a second filter controller 66, a second primary filter 68 and a second secondary filter 70. The second filter controller 66 receives the second voice signal 58 and the second compensation signal 54. The second primary filter 68 receives and filters the second ear canal output signal 48 and feeds a primary filter output signal 65 to the second secondary filter 70 and the second filter controller 66. The second secondary filter 70 filters the primary filter output signal 65 according to second control signal 65C from the second filter controller 66 and feeds a secondary filter output signal 65B as output from the second compensation module (second compensation signal 54). The second control signal 72 sets or controls primary filter coefficients of the second secondary filter 70. The second primary filter 68 is a static Infinite Impulse Response (IIR) filter, wherein primary filter coefficients of the second primary filter 68 are static. The second secondary filter 70 is an adaptive Finite Impulse Response (FIR) filter. The combination of an IIR filter and a FIR filter provides a power-efficient and improved modelling of the ear canal response. Secondary filter coefficients of the second secondary filter 70 are controlled by the second filter controller 66 based on the second voice signal 58 and the primary filter output signal 65 from the second primary filter 68.

Figure 4:
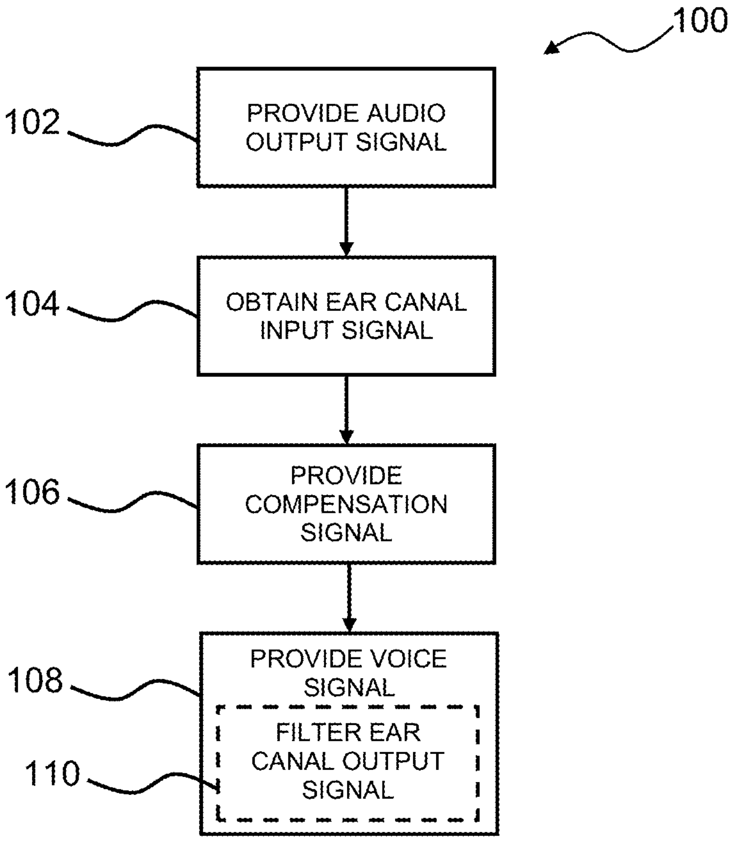
FIG. 4 is a flow diagram of an exemplary method according to the disclosure.

FIG. 4 shows a flow diagram of an exemplary method 100 for estimating a voice signal of a hearing protection system user, the method 100 comprising providing 102 an audio output signal, e.g. first audio output signal 20, based on an ear canal output signal, e.g. first ear canal output signal 22. The method 100 comprises obtaining 104 an ear canal input signal, e.g. first ear canal input signal 16, with an ear canal microphone, e.g. first ear canal microphone 14, and providing 106 a compensation signal, e.g. first compensation signal 28, based on the ear canal output signal, e.g. first ear canal output signal 22. Further, the method 100 comprises providing 108 a voice signal, e.g. first voice signal 32, based on the ear canal input signal and the compensation signal, e.g. first ear canal input signal 16 and first compensation signal 28. In the method 100, providing 108 a compensation signal optionally comprises filtering 110 the ear canal output signal, e.g. first ear canal output signal 22, with a primary filter, e.g. first primary filter 62, and with a secondary filter, e.g. first secondary filter 64. The primary filter, e.g. first primary filter 62, is a static filter and the secondary filter, e.g. first secondary filter 64, is an adaptive filter. In the method 100, providing 108 a compensation signal optionally comprises determining if an adaptation criterion, e.g. no own voice detected, is fulfilled, e.g. based on the voice signal, and adapting secondary filter coefficients of the secondary filter, e.g. based on the voice signal, if the adaptation criterion is fulfilled.

Obtaining 104 an ear canal input signal may comprise obtaining a second ear canal input signal 42 with a second ear canal microphone 44. Providing 106 a compensation signal may comprise providing a second compensation signal 54 based on the second ear canal output signal 48. Providing 108 a voice signal may comprise providing a second voice signal 58 based on the second ear canal input signal 42 and the second compensation signal 54. In the method 100, filtering 110 the ear canal output signal may comprise filtering the second ear canal output signal 48 with a second primary filter 68 and a second secondary filter 70. The second primary filter 68 is a static filter and the second secondary filter 70 is an adaptive filter.

Figure 5:
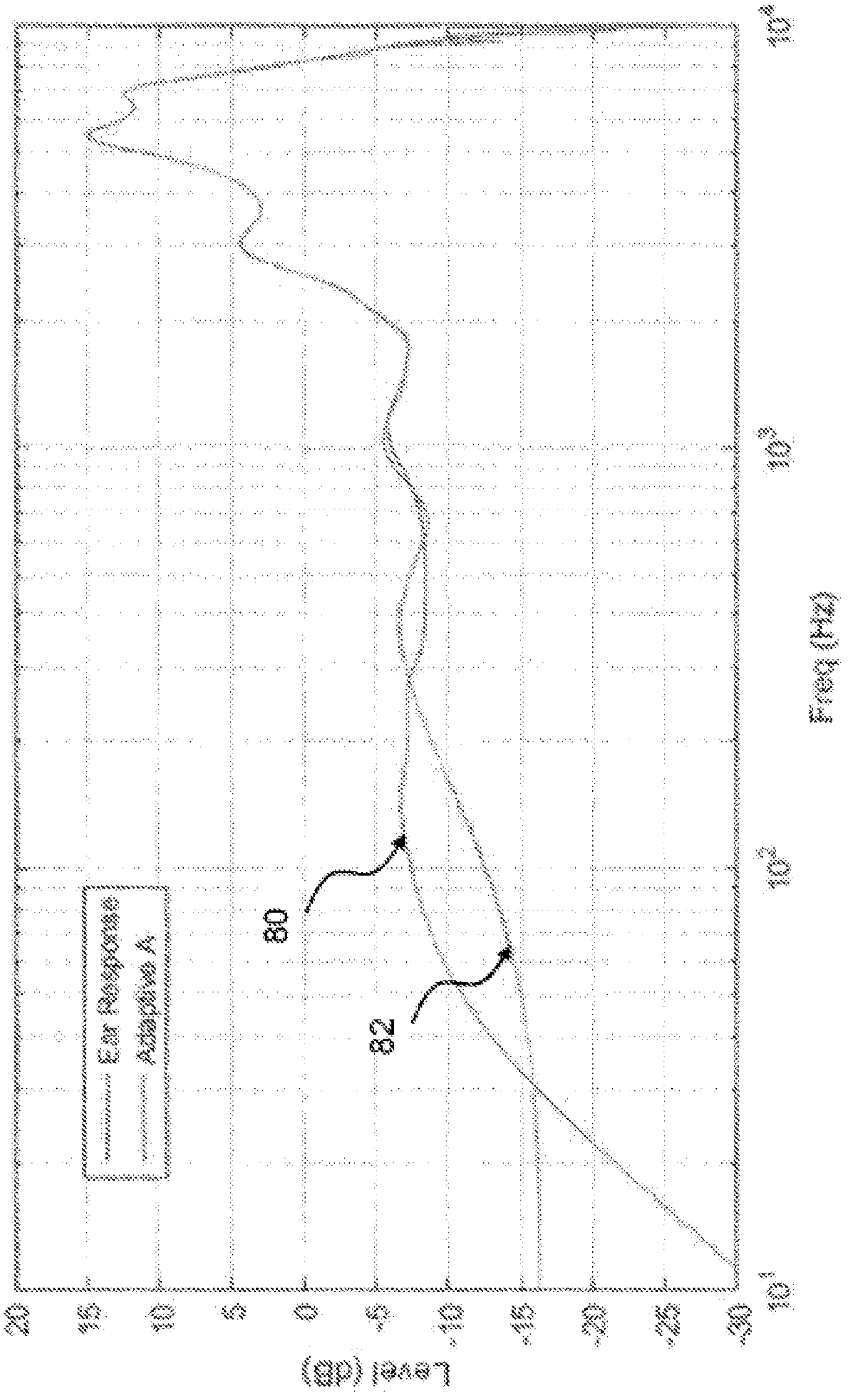
FIG. 5 shows an adaptive filter response with no static filter.

FIG. 5 shows the result of a 42-coefficient typical adaptive filter modelling an ear response (without static filter). The performance of the adaptive filter is poor at low frequencies (less than 500 Hz) with differences between the adaptive filter response 82 (model of ear canal) and the ear canal response 80 (actual ear canal) larger than 5 dB at 100 Hz.

Figure 6:
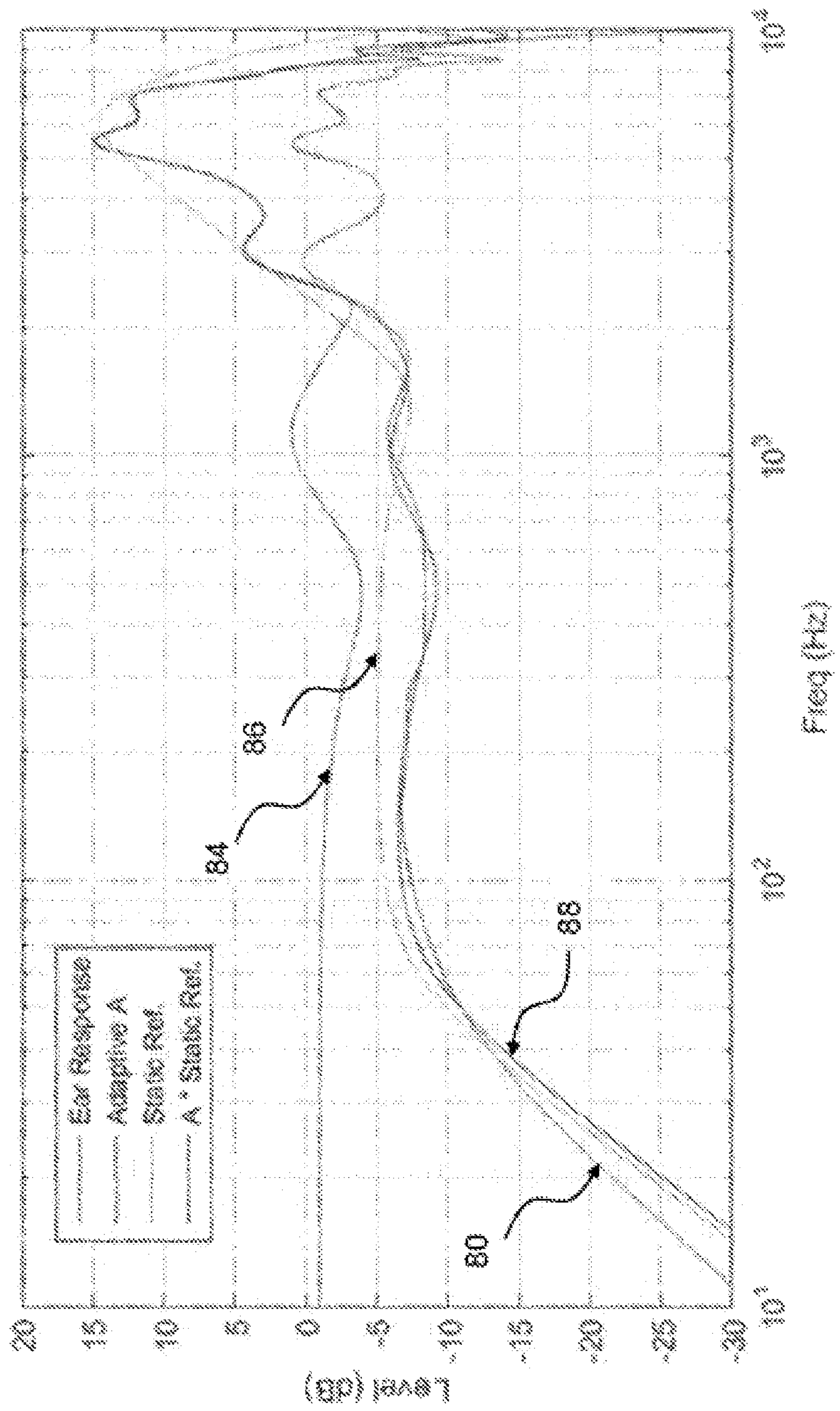
FIG. 6 shows an adaptive filter response combined with static filter.

FIG. 6 shows the result of a 32-coefficient adaptive filter (adaptive filter response 84) with static filter (static filter response 86) modelling the ear canal response 80 (same as in FIG. 5). The combined response 88 of the adaptive filter (e.g. first secondary filter) and the static filter (e.g. first primary filter) shows an improved fit to the ear canal response 80 in particular at low frequencies. Further, the adaptive secondary filter has low gain at high frequencies. Further, the adaptive secondary filter has a relatively small variation in gain, at least up to 8 kHz.

Figure 7:
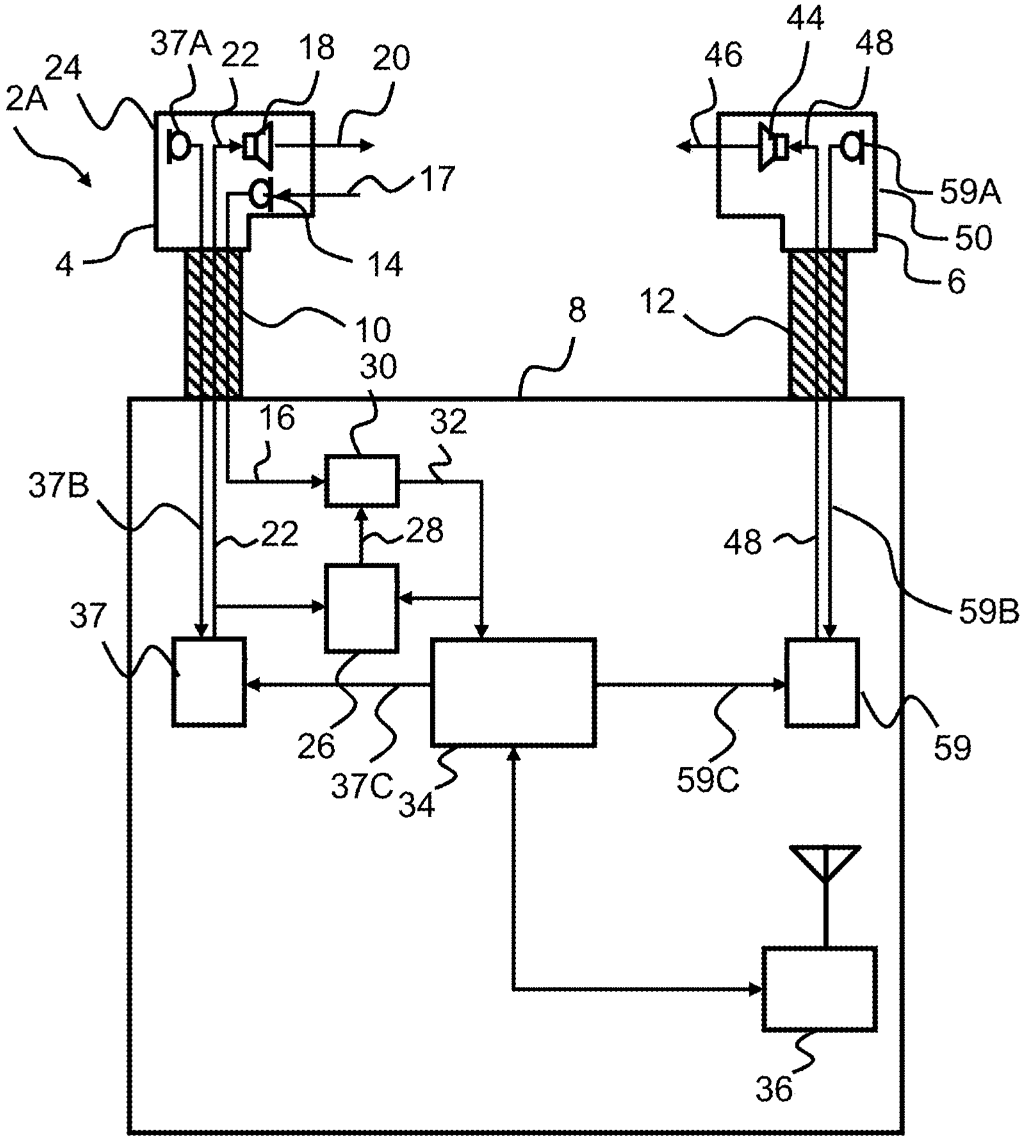
FIG. 7 shows an exemplary hearing protection system.

FIG. 7 shows an exemplary hearing protection system 2A with own voice estimation based on a single ear canal input signal (first ear canal input signal 16).

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES

2, 2A hearing protection system
4 first earpiece
6 second earpiece
8 processing device
10 first cable
12 second cable
14 first ear canal microphone
16 first ear canal input signal
17 first ear canal audio
18 first receiver
20 first audio output signal
22 first ear canal output signal
24 first earpiece housing
26 first compensation module
28 first compensation signal
30 first mixer
32 first voice signal
34 communication unit
36 wireless transceiver unit
37 first hearing protection processing module
37A first external microphone
37B first external input signal
37C first output signal from communication unit
40 second ear canal microphone
42 second ear canal input signal
43 second ear canal audio
44 second receiver
46 second audio output signal
48 second ear canal output signal
50 second earpiece housing
52 second compensation module
54 second compensation signal
56 second mixer
58 second voice signal
59 second hearing protection processing module
59A second external microphone
59B second external input signal
59C second output signal from communication unit
60 first filter controller
62 first primary filter
64 first secondary filter
65 primary filter output signal
65A first control signal
65B secondary filter output signal
66 second filter controller
68 second primary filter
70 second secondary filter
72 second control signal
80 ear canal response
82 adaptive filter response
84 adaptive filter response
86 static filter response
88 combined response of adaptive filter response and static filter response
100 method for estimating a voice signal of a hearing protection system user
102 providing an audio output signal based on an ear canal output signal
104 obtaining an ear canal input signal with an ear canal microphone
106 providing a compensation signal based on the ear canal output signal
108 providing a voice signal based on the ear canal input signal and the compensation signal
110 filtering the ear canal output signal with a primary filter and a secondary filter

The invention claimed is:

1. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the filter coefficient is for modeling a property of the receiver.

2. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the filter coefficient is for modeling a property of the ear canal microphone.

3. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the filter coefficient is for modeling an acoustic property of a sealed ear canal.

4. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the first filter has a constant first gain in a first frequency range from 100 Hz to 500 Hz.

5. The hearing protection system according to claim 4, wherein the first filter is an Infinite Impulse Response (IIR) filter.

6. The hearing protection system according to claim 4, wherein the first filter has a maximum gain in a second frequency range from 4 kHz to 8 kHz.

7. The hearing protection system according to claim 6, wherein the first filter has a local minimum gain in a third frequency range from 1 kHz to 2 kHz.

8. The hearing protection system according to claim 7, wherein the first filter has a linearly increasing gain in a fourth frequency range from 30 Hz to 50 Hz.

9. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the first filter has a maximum gain in a frequency range from 4 kHz to 8 kHz.

10. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the first filter has a local minimum gain in a frequency range from 1 kHz to 2 kHz.

11. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the first filter has a linearly increasing gain in a frequency range from 30 Hz to 50 Hz.

12. A hearing protection system comprising:

an ear canal microphone configured to provide an ear canal input signal;

a receiver configured to provide an audio output signal based on an ear canal output signal;

a compensation module configured to provide a compensation signal based on the ear canal output signal; and a mixer connected to the ear canal microphone and the compensation module, the mixer configured to provide a voice signal based on the ear canal input signal and the compensation signal;

wherein the compensation module comprises a filter controller, a first filter and a second filter, wherein the first filter comprises a filter coefficient, wherein the second filter is an adaptive filter, and wherein the filter controller is configured to control the second filter based on the voice signal; and wherein the filter controller comprises a voice detector configured to detect if a user's own voice is present, and wherein the filter controller is configured to deactivate adaptation of a filter coefficient of the second filter if the voice detector detects a presence of the user's own voice.

13. The hearing protection system according to claim 12, wherein the filter controller is configured to activate adaptation of the filter coefficient of the second filter if the voice detector detects the presence of the user's own voice.

14. The hearing protection system according to claim 4, wherein the first filter is a static filter.

15. A method for providing a voice signal in a hearing protection system, the method comprising:

providing an audio output signal based on an ear canal output signal;

obtaining an ear canal input signal with an ear canal microphone;

providing a compensation signal based on the ear canal output signal; and providing a voice signal based on the ear canal input signal and the compensation signal;

wherein the act of providing the compensation signal comprises filtering the ear canal output signal with a first filter and a second filter, wherein the second filter is an adaptive filter; and wherein the first filter comprises a filter coefficient for modeling a property of a receiver of the hearing protection system.

16. A method for providing a voice signal in a hearing protection system, the method comprising:

providing an audio output signal based on an ear canal output signal;

obtaining an ear canal input signal with an ear canal microphone;

providing a compensation signal based on the ear canal output signal; and providing a voice signal based on the ear canal input signal and the compensation signal;

wherein the act of providing the compensation signal comprises filtering the ear canal output signal with a first filter and a second filter, wherein the second filter is an adaptive filter; and wherein the first filter comprises a filter coefficient for modeling a property of the ear canal microphone.

17. A method for providing a voice signal in a hearing protection system, the method comprising:

providing an audio output signal based on an ear canal output signal;

obtaining an ear canal input signal with an ear canal microphone;

providing a compensation signal based on the ear canal output signal; and providing a voice signal based on the ear canal input signal and the compensation signal;

wherein the act of providing the compensation signal comprises filtering the ear canal output signal with a first filter and a second filter, wherein the second filter is an adaptive filter; and wherein the filter coefficient is for modeling an acoustic property of a sealed ear canal.

18. The method according to claim 15, wherein the act of providing the compensation signal comprises adapting a filter coefficient of the second filter based on the voice signal.

19. The method according to claim 15, wherein the first filter is a static filter.

20. The method according to claim 15, wherein the first filter is an Infinite Impulse Response (IIR) filter.

21. The method according to claim 15, wherein the second filter is a Finite Impulse Response (FIR) filter.

22. The method according to claim 16, wherein the act of providing the compensation signal comprises adapting a filter coefficient of the second filter based on the voice signal.

23. The method according to claim 16, wherein the first filter is a static filter.

24. The method according to claim 16, wherein the first filter is an Infinite Impulse Response (IIR) filter.

25. The method according to claim 16, wherein the second filter is a Finite Impulse Response (FIR) filter.

26. The method according to claim 17, wherein the act of providing the compensation signal comprises adapting a filter coefficient of the second filter based on the voice signal.

27. The method according to claim 17, wherein the first filter is a static filter.

28. The method according to claim 17, wherein the first filter is an Infinite Impulse Response (IIR) filter.

29. The method according to claim 17, wherein the second filter is a Finite Impulse Response (FIR) filter.

30. The hearing protection system according to claim 4, wherein the second filter is a Finite Impulse Response (FIR) filter.

31. The hearing protection system according to claim 4, further comprising a hearing protection processing module and an external microphone, the hearing protection processing module connected to the external microphone for receiving an external input signal from the external microphone, wherein the hearing protection processing module is configured to provide an external output signal based on the external input signal, and wherein the ear canal output signal is based on the external output signal.

32. The hearing protection system according to claim 12, wherein the first filter is an Infinite Impulse Response (IIR) filter.

33. The hearing protection system according to claim 12, wherein the second filter is a Finite Impulse Response (FIR) filter.

34. The hearing protection system according to claim 12, further comprising a hearing protection processing module and an external microphone, the hearing protection processing module connected to the external microphone for receiving an external input signal from the external microphone, wherein the hearing protection processing module is configured to provide an external output signal based on the external input signal, and wherein the ear canal output signal is based on the external output signal.

* * * * *